United States Patent [19]

Eckert et al.

[11] Patent Number: 4,722,941
[45] Date of Patent: Feb. 2, 1988

[54] READILY ABSORBABLE PHARMACEUTICAL COMPOSITIONS OF PER SE POORLY ABSORBABLE PHARMACOLOGICALLY ACTIVE AGENTS AND PREPARATION THEREOF

[75] Inventors: Theodor Eckert; Fritz H. Kemper, both of Muenster; Martin Wischniewski, Neustadt a. Rbge.; Reinhard Hempel, Hanover, all of Fed. Rep. of Germany

[73] Assignee: Kali-Chemie Pharma GmbH, Hanover, Fed. Rep. of Germany

[21] Appl. No.: 911,165

[22] Filed: May 31, 1978

[51] Int. Cl.[4] .................. A61K 31/40; A61K 31/195; A61K 31/415; A61K 47/00

[52] U.S. Cl. ..................... 514/784; 514/221; 514/653; 514/420; 514/535; 514/534; 514/258; 514/786; 514/946

[58] Field of Search ............... 424/180, 244, 258, 265, 424/365

[56] References Cited

U.S. PATENT DOCUMENTS

| | | | |
|---|---|---|---|
| 3,551,554 | 12/1970 | Herschler | 424/4 |
| 3,767,801 | 10/1973 | Tuma et al. | 424/365 |
| 3,772,446 | 11/1973 | Larsson | 424/365 |
| 4,151,304 | 4/1979 | Evans | 424/180 |
| 4,202,888 | 5/1980 | Eckert et al. | 514/26 |
| 4,230,702 | 10/1980 | Eckert et al. | 514/171 |
| 4,250,169 | 2/1981 | Hosoi et al. | 424/DIG. 15 |
| 4,263,313 | 4/1981 | Eckert et al. | 514/558 |

FOREIGN PATENT DOCUMENTS

| | | | |
|---|---|---|---|
| 2357389 | 11/1973 | Fed. Rep. of Germany | 424/180 |
| 1432784 | 4/1976 | United Kingdom | 424/180 |

*Primary Examiner*—Ronald W. Griffin
*Attorney, Agent, or Firm*—Schwartz, Jeffery, Schwaab, Mack, Blumenthal & Evans

[57] ABSTRACT

A readily absorbable pharmaceutical composition of pharmacologically active agents, which per se are poorly absorbable, is disclosed which comprises a pharmacologically effective amount of at least one such pharmacologically active agent distributed in a vehicle comprising an absorption-enhancing amount of at least one fatty acid of medium chain length. The preparation is suited for formulating pharmacologically active bases, cardiac glycosides, steroids, antibiotics, sympathicomimetica, tranquilizing agents, or local anaesthetics.

21 Claims, No Drawings

READILY ABSORBABLE PHARMACEUTICAL COMPOSITIONS OF PER SE POORLY ABSORBABLE PHARMACOLOGICALLY ACTIVE AGENTS AND PREPARATION THEREOF

BACKGROUND OF THE INVENTION

The present invention relates to readily absorbable pharmaceutical formulations of pharmacologically active agents, in particular bases, which are poorly absorbable per se, and to a method for preparing such formulations.

It is well known in the art that in order to obtain a similar pharmacological effect, a number of pharmacologically active agents require considerably higher dosages if administered in oral, rectal, or percutaneous dosage form than if administered parenterally by means of injection. This is an indication that such pharmacologically active agents are absorbed only to a low extent from these formulations.

Yet, there is a need for pharmaceutical formulations which provide such per se poorly absorbable pharmacologically active agents not only in an injectable formulation, but also in orally and/or rectally and/or percutaneously applyable formulations which provide a high degree of enteral absorption of these pharmacologically active agents.

Various methods for improving the absorbability of such insufficiently absorbable pharmacologically active ingredients are known in the art. In some cases the absorbability can be improved by means of a technological treatment of the pharmacologically active agent, e.g., by means of micronization, complex-formation, or addition of solubility improving additives. Yet, these techniques exhibit a number of disadvantages.

Special apparatuses or additional process steps during the preparation and/or formulation process are required for some of these methods; or only a limited number and amount of additives can be applied in certain cases due to safety and/or compatability problems. Furthermore, these techniques can successfully be applied only to a limited number of groups of pharmacologically active agents.

Recently, glycerides of fatty acids of medium chain length, containing from about 6 to about 12 carbon atoms, have been used as carrier materials for pharmacologically active ingredients. Yet only a very limited group of pharmacologically active agents can be satisfactorily formulated using triglycerides a a carrier material, due to a poor solubility of most pharmacologically active ingredients in such a carrier material. In particular, various difficulties are encountered, if pharmacologically active bases are to be formulated with glycerides, since these compounds are not sufficiently stable in free base form, and in salt form are not sufficiently soluble.

SUMMARY OF THE INVENTION

It is an object of the present invention to provide enteral and topical pharmaceutical formulations of pharmacologically active agents which per se are poorly absorbable, which provide for a high degree of enteral or percutaneous absorption of such pharmacologically active agents.

It is a further object of the present invention to provide such an enteral formulation wherein the enteral absorption of the per se poorly absorbable pharmacologically active agents is increased sufficiently to permit an enteral application of these pharmacologically active agents.

It is a special object of the present invention to provide such a formulation of per se poorly absorbable pharmacologically active bases, in particular aliphatic and/or heterocyclic amines.

It is a further special object of the present invention to provide such a formulation of per se poorly absorbable cardiac glycosides, in particular of g-strophanthin, k-strophanthin, or proscillaridin, preferably such a formulation wherein the enteral absorption of poorly absorbable glycosides is sufficiently high to insure a constant degree of absorption of such glycosides after enteral application.

It is a further special object of the present invention to provide such a formulation of per se poorly absorbably steroids, e.g., steroid hormones and derivatives thereof, in particular pregn-4-ene-3,20-diones and pregna-4,6-diene-3,20-diones, such as progesterone, medrogestone and similar gestagenes.

It is a further special object of the present invention to provide such a formulation of per se poorly absorbable antibiotics, such as griseofulvin.

It is a further special object of the present invention to provide such a formulation of per se poorly absorbable tranquilizers, e.g., benzodiazepine derivatives.

It is a further object of the present invention to provide such a formulation of per se poorly absorbable sympathicomimetica, such as (hydroxphenyl)-ethanolamine derivatives or indol derivatives.

It is a further object of the present invention to provide such a formulation of per se poorly absorbable local anaesthetics such as procaine.

It is a further object of the present invention to provide such a formulation of per se poorly absorbable antispasmodics, e.g., antispasmodically active dialkylaminoethanol derivatives, for example, bencyclane or valethamate-bromide.

It is a further special object of the present invention to provide such a formulation of per se poorly absorbably antiinflammatory agents such as indomethacine.

It is a further object of the present invention to provide such a formulation of per se poorly absorbable coronary therapeutic, in particular, coronary vasodilators, such as dipyridamole.

It is a further object of the present invention to provide topical pharmaceutical formulations of pharmacologically active agents which ensure a ready penetration from the site of application into the skin, preferably into the deeper layers thereof, and/or a permeation through the skin and absorption into the body system.

It is a further object of the present invention to provide such a topical formulation of primarily locally effective pharmacologically active agents, such as antiinflammatory agents, analgesics, local anaesthetics, and antirheumatics, which provide for an increased speed and degree of permeation.

It is a further object of the present invention to provide such a topical formulation of primarily systemically-effective pharmacologically active agents (which upon enteral application are largely normally destroyed in the gastric-intestinal tract and/or in the liver) which provide for a sufficiently high speed and degree of permeation and absorption of these systemically-effective agents through the skin to permit a cutaneous application thereof.

In order to accomplish the foregoing objects and advantages of the present invention, there is provided a readily absorbable pharmaceutical composition which comprises a pharmacologically effective amount of at least one per se poorly absorbable pharmacologically active agent distributed in a vehicle comprising an absorption enhancing amount of at least one fatty acid of medium chain length.

The preparation according to the present invention is preferably suited for formulating per se poorly enterally and/or percutaneously absorbable pharmacologically active bases, e.g., pharmacologically active compounds including a basic mono-, di-,or trisubstituted aliphatic or heterocyclic amino group in their molecule.

Preferably, the vehicle further comprises at least one glyceride of a fatty acid of medium or long chain length.

According to the present invention, there is further provided a process for preparing a readily absorbable pharmaceutical composition of a per se poorly absorbable pharmacologically active agent which comprises the step of dissolving the agent in a vehicle comprising at least one fatty acid of medium chain length.

According to the present invention, there is further provided a method of enteral or percutaneous medication which comprises enterally, preferably orally, or percutaneously administering the above described pharmaceutical composition to a larger mammal.

DETAILED DESCRIPTION OF THE INVENTION AND ITS PREFERRED EMBODIMENTS

It has been found that fatty acids of medium chain length exhibit an unexpectedly high dissolution capacity for many pharmacologically active agents, in particular, pharmacologically active bases, and that surprisingly not only the solubility but also the enteral and/or percutaneous absorbability of these agents is highly increased in the presence of fatty acids of medium chain length. By dissolving the pharmagologically active agent in a vehicle containing fatty acids of medium chain length, its lipophilic properties are increased and its absorption, e.g., through the intestinal mucosa, is increased. The beneficiary effect of the resulting improved absorption is further increased by the fact that, contrary to fatty acids of long chain length, fatty acids of medium chain length are transported into the major circular system directly through the portal vein instead of passing through the lymphatic system. Thus, the pharmacologically active agents also can reach their site of action more rapidly and under less loss.

Fatty acids of medium chain length comprise fatty acids, preferably saturated monocarboxylic acids, having a chain length of preferably between about 6 and about 12, most preferably between about 8 and about 10 carbon atoms, and mixtures thereof. Especially suited are capric and caprylic acid and mixtures thereof. Of course, these fatty acids may be used either singly or in form of mixtures thereof, wherein the ratio between the various acids can take any desired value.

The compositions according to the present invention may further comprise fatty acids having a chain length of from about 12 to about 18 carbon atoms. The addition of such fatty acids of long chain length may be advisable in some cases in order to obtain a desirable consistency and/or melting range of the composition.

According to a preferred embodiment of the invention, the composition further comprises glycerides of fatty acids in addition to the pharmacologically active agent and the fatty acid of medium chain length. In this manner, the good dissolution capacity of the fatty acids of medium chain length can be further increased for some of the pharmacological agents, in particular if partial glycerides of fatty acids of medium or long chain length are used.

Partial glycerides of fatty acids of medium and long chain length comprise mono- and diglycerides of saturated and/or unsaturated fatty acids, having a chain length of between about 6 and about 18 carbon atoms, and mixtures thereof. Especially suited are mono- and diglycerides of capric, caprylic, oleic, palmitic, and stearic acids and mixtures thereof. There are no limitations as to what the ratio between various glycerides in glyceride mixtures may be. The proportions of glycerides in the composition therefore may be choosen to best suit the desired properties of the composition depending on the type and consistency of the formulation and its intended mode of application, the type and amount of the pharmacologically active agents, and the type and amount of fatty acids of medium chain length which are present in the composition, and commercial availability of the respective glycerides or fatty acids.

The term "pharmacologically active agent" as used in the present specification and claims is meant to denote agents which are effective in larger mammals, in particular human beings, in treating or preventing diseases and/or disorders in the body functions and/or influencing the state of the body and its function in a desirable manner.

The term "per se poorly absorbable" as used in the present specification and claims is meant to denote such agents, which upon being enterally or cutaneously applied in a solid or liquid formulation devoid of any dissolution and/or absorbability improving additives exhibit such a low and/or slow per se absorability, that by means of enteral or topical administration, a pharmacologically effective level in the body of larger mammals cannot be reached or can be reached only by administering a dosage which corresponds to at least 2 times the parenterally effective dosage of the respective agent, or that in the case of enteral application only less than 50% of the enteral dosage which is necessary to achieve a pharmacologically effective level of the respective agent in the body are actually absorbed in the gastro-intestinal tract.

Whether the actual per se absorbability of a respective pharmacologically active agent is sufficient or insufficient, of course, will depend on the chemical and physical properties of said agent, especially the kind and degree of its pharmacological activity as well as the desired pharmacological effect.

Enteral formulations according to the present invention are suited for enteral application of pharmacologically active agents which per se ar poorly absorbable from the gastro-intestinal tract.

Topical formulations according to the present invention ar suited for cutaneous application of such pharmacologically active agents which exhibit a primarily local activity in the body near the site of their application, yet which per se exhibit an unsatisfactorily slow and/or poor penetration into and/or permeation through the skin. Topical compositions according to the present invention are also suited for applying such pharmacologically active agents which possess a primarily systemic activity, yet which upon oral administration exhibit undesirable side effects in the gastro-intestinal tract and/or which are at least partially destroyed in the gastro-intestinal tract.

Poorly absorbable pharmacologically active agents, which are advantageously applied in form of a formulation according to the present invention, include pharmacologically active bases, in particular amines, cardiac glycosides, steroids, antibiotics, spasmolytica, agents which are effective in improving coronary disorders, anti-inflammatory agents, sympathicomimetica, tranquilizers, and local anaestetics.

The term "cardiac glycosides", as it is used in the present application, includes cardiotonically active glycosides containing a cardenolidor bufadienolid aglycon, which is substituted in the 3-position by a glycosidic group containing 1 to 4 sugar units, and semi-synthetical derivatives thereof. The sugar units may be pentose or hexose units or partial reduction products thereof.

Cardiotonically active semi-synthetic derivatives of naturally-occuring cardiac glycosides include the aglycones themselves, glycosides wherein the original number of sugar units is reduced, glycosides wherein the glycosidic group and/or the aglycon are chemically modified by etherification or esterification of at least part of the hydroxy groups with lower alkyl or lower carboxylic acyl, hydroxylation or dehydrogenation.

Among the cardiac glycosides with cardenolid structure, there may be cited the digitalis glycosides which occur naturally in digitalis purpurea and digitalis lanata and derivatives thereof, e.g., lanatosids A, B, or C, purpurea glycosides A or B, digitoxin, digoxin or gitoxin or the aglycons thereof, k-strophanthus glycosides which occur naturally in strophanthus kombe, g-strophanthus glycosides which occur naturally in strophanthus gratus, e.g., k-strophanthins $\alpha,\beta$, and $\gamma$ containing the aglycon k-strophanthidin ($=3\beta$, 5,14-trihydroxy-19-oxo-5$\beta$-card-20(22)-enolid) and g-strophanthin containing the aglycon g-strophanthidin ($=1\beta,3\beta,5,11\alpha,14,19$-hexahydro-5$\beta$-card-20(22)-enolid).

Among the cardiac glycosides with bufadienolid structures, there may be cited the squill glycosides which occur naturally in scilla martima, e.g., proscillaridin, scillaren A, scillaren B.

Preparations according to the present invention are especially suited for the enteral application of such cardiac glycosides which per se are particularly poorly enterally absorbable, for example, cardiac glycosides of which only about 5% or less, e.g., between about 5 and 0.3% are enterally absorbed. Examples of per se poorly enterally absorbable cardiac glycosides are g-strophanthin, k-strophanthin and proscillaridin.

The concentration of the cardiac glycoside in the enteral preparations according to the present invention may vary considerably depending on the physical and chemical properties, especially the pharmacological activity of the respective cardiac glycoside which is used, on its enteral absorbability per se, and on its sensitivity to metabolic decompositions in the gastro-intestinal tract and/or the liver, as well as on the amount of absorption enhancing fatty acids of medium chain length and partial glycerides present in the preparation and the contemplated mode of administration, the treated condition and the therapy which is desired. Usually, a satisfactory enteral activity is obtained with an amount corresponding to between about 1 and about 3 times, preferably about 1 and about 2 times the parenterally-effective amount of the respective cardiac glycosides. For example, enterally-effective amounts of g-strophanthin, k-strophanthin or proscillaridin within the compositions according to the present invention are between about 0.1 and about 0.3, preferably about 0.2 and 0.25 mg per single dosage unit.

Preparations according to the present invention are also suited for the application of steroids which per se are particularly poorly absorbable.

The term "steroids" as it is applied in the present application includes steroid hormones, in particular gestagene hormones, and synthetic and semi-synthetic derivatives thereof, especially pregn-4-ene-3,20-diones and pregna-4,6-diene-3,20-diones. Examples of per se poorly enterally absorbable steroids are progesterone and medrogestone.

The pharmacological properties of the steroids and the medical application thereof are well known in the art.

The concentration of the steroid in preparations according to the present invention may vary considerably depending on the physical and chemical properties, especially the pharmacological activity of the respective steroid which is used, and on its absorbability per se, as well as on the amount of absorption enhancing fatty acids of medium chain length and partial glycerides present in the preparation and the contemplated mode of administration, the treated condition and the pharmacological effect which is desired. Usually a satisfactory enteral activity is obtained with an amount corresponding to between about 1 and about 3 times, preferably about 1 and about 2 times the parenterally effective amount of the respective steroid. For example, enterally-effective amounts of progesterone or medrogestone within the compositions according to the present invention are between about 2 and about 50 mg per single dosage unit.

Preparations according to the present invention are also suited for the application of antibiotics which are per se poorly absorbable, for example, griseofulvin.

The concentration of griseofulvin preparations according to the present invention may vary considerably depending on the amount of absorption enhancing fatty acids of medium chain length and partial glycerides present in the preparation and the contemplated mode of administration, the treated condition and the pharmacological effect which is desired. Usually a satisfactory antibiotic activity is obtained in enteral and topical compositions containing between about 50 and about 150 mg of griseofulvine per single dosage unit.

Preparations aocording to the present invention are also suited for the application of sympathicomimetically active agents which are per se poorly absorbable, for example, phenylalkanolamine derivatives such as N-(lower alkyl)phenyl-ethanolamines and propanolamines wherein the phenyl may be substituted by 1 or 2 hydroxy groups, e.g., synephrine.

The concentration of the sympathicomimetic agent in the preparations according to the present invention may vary considerably depending on the physical and chemical properties, especially the pharmacological activity of the respective agent which is used, and on its absorability per se, as well as on the amount of absorption enhancing fatty acids of medium chain length and partial glycerides present in the preparation and the contemplated mode of administration, the treated condition and the pharmacological effect which is desired. For example, in the case of enteral formulation of synephrine, the amount per single dosage unit preferably is between about 20 and about 60 mg.

Preparations according to the present invention are also suited for the application of tranquilizers, especially benzodiazepine derivatives, such as diazepam or 7-chloro-1-methyl-2-(hydroxymethyl)-5-(2'-chlorophenyl)-1H-2,3-dihydro-14-benzodiazepine. The amount of these tranquilizing benzodiazepine derivatives in enteral compositions according to the present invention suitably is between about 5 and about 25 mg per single dosage unit.

Preparations according to the present invention are also suited for the application of antispasmodically active agents, for example, antispasmodically active di-loweralkylaminoethyl ester and ether derivatives, e.g., valethamate-bromide or bencyclane.

The concentration of the spasmolytically active agents in the preparations according to the present invention may vary considerably depending on the physical and chemical properties, especially the pharmacological activity of the respective agent which is used, and on its absorbability per se, as well as on the amount of absorption enhancing fatty acids of medium chain length and partial glycerides present in the preparation and the contemplated mode of administration, the treated condition and the pharmacological effect which is desired. Enteral preparations of bencyclane for example may comprise an amount of from about 25 to about 100 mg per single dosage unit.

Preparations according to the present invention are also suitable for the application of agents which are effective in preventing and/or ameliorating coronary disorders or insufficiencies, for example, coronary vasodilators such as dipyridamole.

Preparations according to the present invention are also suitable for the applications of anti-inflammatory agents such as indomethacine or local anaesthetics such as procaine.

Basic pharmacologically active agents may be incorporated into the compositions according to the present invention in free base form or in form of a salt with a pharmaceutically acceptable acid, preferably a fatty acid containing from about 6 to about 18, preferably from about 6 to about 12 carbon atoms.

According to a preferred embodiment of the present invention, the composition comprises a pharmacologically effective amount of a pharmacologically active base, only such an amount of a fatty acid of medium chain length which essentially is sufficient to form an acid addition salt of the basic pharmacologically active agent and at least one glyceride, preferably a partial glyceride.

The amount of absorption enhancing fatty acids of medium chain length in the preparations according to the present invention, which is effective to sufficiently enhance the enteral or percutaneous absorption to permit an enteral or cutaneous administration of the per se poorly absorbable pharmacologically active agent may vary considerably depending on the per se absorbability of the respective agent, as well as on the chemical and physical properties of any other ingredients of the composition, in particular on its content in partial glycerides. Typically, satisfactory results are obtained with preparations wherein the total amount of fatty acids of medium chain length and of partial glycerides is between about 20 and about 100%, preferably about 40 and about 100% of the vehicle.

The enteral formulations according to the present invention, may take the form of solid or liquid formulations for oral or rectal application. Thus, the formulations may be in the form of capsules, tablets, coated tablets, suppositories, or emulsions.

The topical formulations according to the present invention may take the form of compositions having a semisolid consistency, such as ointments, creams, jellies, foams, aerosols, or the like, or the form of liquid solutions, suspensions, and emulsions, preferably in non-aqueous solvents.

Depending on the type of the pharmacological agent therein, the desired consistency and the contemplated mode of application, the carrier material in the vehicle composition according to the present composition may essentially consist of only the fatty acids of medium chain length or of mixtures of these acids with partial glycerides of fatty acids of medium and long chain length or may comprise additional carrier materials. These formulations can easily be prepared according to the present invention, since the partial glycerides which are utilized according to the present invention comprise partial glycerides which at room temperature are liquid as well as such partial glycerides which at room temperature are solid. By mixing the appropriate partial glycerides, nearly any desired consistency can be obtained and/or a melting point which is suitable for rectally applied suppositories can be achieved.

If desired, enteral formulations may further comprise conventional pharmaceutical carriers and additives, for example, viscosity-improving and/or structure- or matrix-forming additives which provide for an appropriate viscosity and physical structure. Suitable such additives are, e.g., inorganic or organic thickening and structure-forming agents such as saturated higher fatty acids and alcohols containing, e.g., 12 to 20 carbon atoms, for example, stearic or palmitic acid, stearic or cetylic alcohol, waxes like beeswax, synthetic esters of higher fatty acids and higher fatty alcohols, or partial glycerides of fatty polyhydroxy acids (e.g., the commercial product "Softigen 701"). Suppositories may further contain any conventional water soluble or fatty suppository bases as additional vehicles. The compositions may further comprise pharmaceutical adjuvants, e.g., binders or lubricants for tabletting, stabilizing-, flavoring-, or emulsifying agents or preservatives.

If the pharmacologically active ingredients within the enteral composition are sensitive to strong acids, it may be advisable to apply an enteric coating to the oral dosage forms, e.g., gelatin capsules, of such agents.

Topical formulations according to the present invention may further comprise additional carriers, such as pharmacologically-acceptable oils and wax, and/or such supplementary pharmaceutical adjuvants which are conventionally used in topical formulations, e.g., in conventional bases for ointments, creams, and jellies. In many cases it may be advisable to incorporate a structure-forming, thickening or gel-forming agent into the composition. Suitable such agents are, in particular, highly dispersed silicic acid (e.g., the commercial product "Aerosil"), bentonites, modified montmorillonites, such as alkyl ammonium salts of montmorillonites (e.g., the commercial products "Bentone"), wherein the alkylgroups may contain 1 to 20 carbon atoms, e.g., di-methyl-dialkyl-ammonium salts wherein the alkylgroups contain 16 to 18 carbon atoms, organic structure-forming, thickening and suspending agents, e.g., cetostearylic alcohol and modified castor oil products (e.g., the commercial product "Antisettle CVP" ®)). Creams may be in the form of emulsions, which may contain conventional pharmaceutically-acceptable emulsifying agents.

The formulations according to the present invention are prepared in any conventional manner, e.g., by dissolving the per se poorly absorbably pharmacologically active agents in the fatty acids of medium chain length, optionally adding additional adjuvants, and formulating the resulting mixture into the desired dosage form by known pharmaceutical methods, e.g., tabletting, molding into suppositories, or filling into capsules.

If a basic pharmacologically active agent is formulated together with a salt-forming amount of the fatty acid of medium chain length and glycerides, it is not necessary to separately prepare a salt of the base and the fatty acid and subsequently dissolve this salt in the glycerides. Yet, according to a preferred embodiment of the process, the free base is dissolved in a mixture of the fatty acid and the glycerides, preferably partial glycerides. In this case the free fatty acid in the mixtures serves to form an acid addition salt with the pharmacologically active base.

The high enteral absorption of the formulations according to the present invention is demonstrated by determination of the level of the respective pharmacological agents in the blood and determination of the amount of the pharmacologically active agent which is excreted through the kidneys.

The level of 7-chloro-1-methyl-2-(hydroxymethyl)-5-)2'-chlorophenyl)-1H-2,3-dihydro-14-benzodiazepine (which in the following will be abbreviated as "tranquilizer KC 1956") in the blood after oral application has been determined in humans.

The blood level values of tranquilizer KC 1956 which indicate the degree of its bioavailability from the applied compositions have been determined after oral application of the tranquilizer in form of a conventional composition and in form of a composition according to the present invention.

The following compositions are used:

| (a) Capsules A: containing KC 1956 in a conventional formulation | |
|---|---|
| KC 1956 micronized | 10 mg/capsule |
| Lactose (D 80) | 121 mg/capsule |
| Corn starch | 57 mg/capsule |
| Gelatin | 2 mg/capsule |
| Primojel+ | 8 mg/capsule |
| Magnesium stearate | 2 mg/capsule |
| Total | 200 mg/capsule |

| (b) Capsules B: containing KC 1956 in a composition according to the present invention | |
|---|---|
| KC 1956 | 10.0 mg/capsule |
| Capric acid | 29.0 mg/capsule |
| Imvitor 742 ®++ | 261.0 mg/capsule |
| Total | 300.0 mg/capsule |

+carboxymethylstarch (Manufacturer Verenigde Zetmeelbedrijven "De Bijenkorf" N.V.)
++highly purified mixture of mono- and diglycerides of oleic acid comprising about 40% of monoglyceride and about 60% of diglyceride (Manufacturer Dynamit Nobel AG.).

Capsules A contain the tranquilizer KC 1956 in micronized form, that is the form that is the best absorbable form acording to the present state of the art. Capsules B contain the tranquilizer KC 1956 in a composition according to the present invention, comprising an amount of fatty acid of medium chain length which is sufficient to form fatty acid addition salts of KC 1956 and a mixture of partial glycerides.

10 mg of the tranquilizer in form of the above described compositions is administered orally to test persons on an empty stomach, followed by ml of water. Blood samples are taken at ½-hour intervals during the first 3 hours after application and at 5 and 7 hours after application. The amount of KC 1956 in the blood samples is determined by means of gas-chromatography. The results are given in Table I below. In Table I the average blood level values of groups of 6 test persons each for three different modes of application, are given in nanogramm/ml plasma as a function of the time at which the blood samples have been taken.

TABLE I

BLOOD LEVEL OF KC 1956 IN HUMANS IN ng/ml PLASMA AFTER ORAL APPLICATION OF 10 mg OF KC 1956 (N = 6)

| | KC 1956 CAPSULES A | | KC 1956 CAPSULES B | |
|---|---|---|---|---|
| TIME | $\bar{x}$ | $s_{\bar{x}}$ | $\bar{x}$ | $s_{\bar{x}}$ |
| 30 Min. | 10.9 | 1.8 | 24 | 6.9 |
| 1 h | 10.5 | 1.7 | 34 | 4.0 |
| 1.5 h | 6.4 | 0.9 | 24 | 4.6 |
| 2 h | 4.2 | 0.3 | 17 | 5.1 |
| 2.5 h | 3.3 | 0.3 | — | — |
| 3 h | 2.6 | 0.2 | 12 | 3.1 |
| 5 h | 2.4 | 1.1 | 5 | 0.7 |
| 7 h | 1.9 | 1.9 | 4 | 0.7 |

As can be seen from the data in Table I, by means of the formulation according to the present invention (capsule B), the systemic availability of the tranqualizer as well as its maximum blood level are increased to about three times the values which are obtained by means of the conventional composition (capsules A).

The renal excretion of procaine after oral application of procaine contained in a formulation according to the present invention is determined in 3 female test persons in the following cross-test procedure.

The total amount of aromatic diazotizable amino groups in the amount of urine which is collected within 72 hours is determined and serves as a measure of the rate of excretion of procaine.

Firstly, a blank-value from a urine collected within 24 hours is determined for the test persons. Then 25 mg of procaine hydrochloride are administered orally and the total amount of excreted diazotizable aromatic amino groups in the urine collected within 72 hours is determined. The results obtained after subtraction of the blank-value indicate an absorption rate of 50-60% of the administered amount of procaine-hydrochloride.

In the same manner as described above the resorption rate of procaine is determined after oral application of the following procaine-containing compositions according to the present invention:

| | |
|---|---|
| 21.7 mg | Procaine-base (corresponding to 25 mg of procaine hydrochloride) |
| 40 mg | Capric acid |
| 40 mg | Lauric acid |
| 100 mg | Mono-diglyceride mixture of fatty acids of medium chain length ($C_6$-$C_{12}$) |
| 201.7 mg | Total |

The results of this test indicate a total absorption rate of between 80 and 90% of the procaine from this composition, that is an average increase of 54%.

The determination of the amount of diazotizable aromatic amino-groups is carried out as follows:

The total amount which has been excreted within 72 hours is calculated by adding the amounts which are determined in each of the total amounts of urine which are collected in each of the three twenty-four hour periods. 2 ml samples of the urine, which is collected within 24 hours, are added to 3 ml of 1N-NaOH and are heated on a water-bath for a period of 20 minutes. Subsequently, 4 ml of 1N-HCl are added and the mixture is cooled and filled up with water to an amount of 10 ml. 1 ml of a 0.1% sodium nitrite solution are added to 4 ml of the above mixture. The resulting mixture is allowed to stand for a period of 3 minutes, then 1 ml of a 0.5% amidosulfuric acid solution is added, the mixture is thoroughly shaken and again allowed to stand for a period of 3 minutes. Then, 2 ml of a 0.1% solution of N-(naphthyl)-(1))-ethylene-diammonium dichloride is added and subsequently the resulting mixture is filled up with water to an amount of 10 ml. This diluted solution is allowed to stand for 10 minutes and then the extinction at 545 nm is determined. From the results, the total amount of diazotizable amino groups within the total amount of urine collected within 24 hours is calculated and the resulting values are added to obtain the total amount which has been excreted within the 72 hour period.

The invention will now be further illustrated by means of the following examples.

Unless stated otherwise, the term "parts" is meant to denote parts by weight.

EXAMPLE 1

10 g of g-strophanthin are dissolved in 20 kg of a mixture comprising 70 parts of lauric acid and 30 parts of capric acid under heating to a temperature of 40° C. 500 mg portions (corresponding to 0.25 mg of g-strophanthin) of the resulting mixture are filled into gelatin capsules at a temperature which is above the solidification temperature of the mixture of 36° C. The capsules are allowed to solidify and subsequently are provided with an enteric coating in a conventional manner.

EXAMPLE 2

10 g of g-strophanthin are dissolved in 10 kg of a mixture of capric acid and mono-glyceride of oleic acid under heating to a temperature of 40° C. Portions of 250 mg of the resulting mixture (corresponding to 0.25 mg of g-strophanthin) are filled into gelatin capsules at a temperature which is above the solidifying temperature of the mixture of 37° C.

EXAMPLE 3

250 g of medrogestone are dissolved in 2.5 kg of a mixture comprising 40 parts of capric acid and 60 parts of lauric acid under heating to a temperature of 40° C. Portions of 250 mg of the resulting mixture (corresponding to 25 mg of medrogestone) are filled into gelatin capsules at a temperature above the solidifying temperature of the mixture which is 30° C.

EXAMPLE 4

500 g of griseofulvin in micronized form are dissolved or else suspended in 5 kg of a mixture comprising equal parts of capric acid and lauric acid under heating to a temperature of 40° C. The resulting mixture which solidifies at a temperature of 30° C., is micro-encapsulated by means of spray-drying in a conventional manner. The resulting dry powder can be formulated into solid dry dosage forms, such as tablets, pellets, or granulates.

EXAMPLE 5

500 g of griseofulvin in micronized form are dissolved or else suspended in 5 kg of a mixture containing equal parts of capric acid and lauric acid under heating to a temperature of 40° C. The resulting mixture is mixed with 2.5 kg of diglyceride of capric acid, 2 kg of eucerinum anhydricum ® (mixture of wool alcohols in highly purified aliphatic hydrocarbons, Manufacturer Beiersdorf AG) and 0.5 kg of beeswax to obtain an ointment.

EXAMPLE 6

200 g of synephrine-base are dissolved in 800 g of a mixture of capric and lauric acid under heating to a temperature of 40° C. Portions of 250 mg of the resulting mixture (corresponding to 50 mg of synephrine-base) are filled into gelatin capsules at a temperature which is above the solidifying temperature of the mixture of 30° C.

EXAMPLE 7

165 g of synephrine-base and 290 g of caprylic acid are dissolved in 500 g of a mixture of mono- and diglycerides of fatty acids of medium chain length ($C_8$-$C_{10}$), namely the commercial product "Witafrol 7420 ®*. Portions of 239 mg of the resulting mixture (corresponding to 41.25 mg of synephrine-base) are filled into gelatin capsules.

EXAMPLE 8

217 g of procaine-base, 400 g of capric acid, and 400 g of lauric acid are dissolved in 1000 g of a mixture of mono- and diglycerides of fatty acids of medium chain length, namely the commercial product Witafrol 7420 ®*. Portions of 202 mg of the resulting mixture (corresponding to 21.7 mg of procaine-base) are filled into gelatin capsules.

EXAMPLE 9

714 g of bencyclane-base, 650 g of capric acid, and 650 g of lauric acid are dissolved in 1000 g of a mixture of mono- and diglycerides of fatty acids of medium chain length, namely the commercial product Witafrol 7420 ®*. Portions of 211 mg of the resulting mixture (corresponding to 50.0 mg of benzyclane-base) are filled into gelatin capsules.

* Witafrol 7420 ® = mixture of mono- and diglycerides of capric acid and caprylic acid, Manufacturer Dynamit Nobel AG.

EXAMPLE 10

714 g of benzyclane-base, 650 g of capric acid and 650 g of lauric acid are dissolved in 4000 g of a mixture of mono- and diglycerides of fatty acids of medium chain length, namely the commercial product Witafrol 7420 ®*. The resulting solution is incorporated into 13.986 kg of a molten suppository mixture (commercial product Witepsol H 5 ®**) under agitation, and the resulting mixture is molded into suppositories of 2000 mg each (corresponding to 71.4 mg of bencyclane-base).

EXAMPLE 11

100 g of diazepam and 290 g of capric acid are dissolved in 2.61 kg of a mixture of mono- and diglycerides of fatty acids of medium chain length (commercial product Imvitor 742 ®***) at a temperature of 35° C. Portions of 300 mg of the resulting mixture (corresponding to 10 mg of diazepam) are filled into gelatin capsules.

* Witafrol 7420 ®=mixture of mono- and diglycerides of capric and caprylic acid, Manufacturer Dynamit Nobel AG.
** Witepsol H 5 ®=mixture of modified triglycerides of saturated fatty acids, Manufacturer Dynamit Nobel AG.
*** Imvitor 742 ®=highly purified mixture of mono-and diglycerides of capric and caprylic acid, Manufacturer Dynamit Nobel AG.

EXAMPLE 12

100 g of 7-chloro-1-methyl-2-(hydroxymethyl)-5-(2'-chlorophenyl)-1H-2,3-dihydro-14-benzodiazepine (tranquilizer KC 1956) and 290 g of capric acid are dissolved in 2.61 kg of a mixture of mono- and diglycerides of fatty acids of medium chain length (commercial product Imvitor 742 ®***) at a temperature of 35° C. Portions of 300 mg of this mixture (corresponding to 10 mg of the tranquilizer KC 1956) are filled into gelatin capsules.

*** Imvitor 742 ®=highly purified mixture of mono- and diglycerides of capric and caprylic acid, Manufacturer Dynamit Nobel AG.

What is claimed is:

1. A method of enhancing the absorption of an enterally or topically administered pharmacological active agent capable of eliciting a physiological effect in a human or animal subject, said active agent comprising a basic compound selected from the group consisting of antibiotics, antispasmodic agents, agents which are effective in improving coronary disorders, anti-inflammatory agents, sympathicomimetically active agents, tranquilizers and local anaesthetics, which method comprises the step of concurrently administering to the subject an amount of said active agent effective to produce the desired physiological effect and a vehicle comprising an absorption enhancing amount of a free fatty acid of medium chain length containing from about 6 to about 12 carbon atoms.

2. The method as defined in claim 1, wherein the per se poorly absorbable pharmacologically active basic agent is selected from the group consisting of valethamatebromide, bencyclane, dipyridamole, indomethacine, synephrine, diazepam, 7-chlor-1-methyl-2-(hydroxymethyl)-5-(2'-chlorophenyl)-1H-2,3-dihydro-1,4-benzodiazepine and procaine.

3. The method as defined in claim 1, wherein the amount of fatty acids of medium chain length is between about 1 and about 100% weight of the vehicle.

4. The method as defined in claim 3, wherein the total amount of fatty acids of medium chain length is from about 20 to about 100% by weight of the vehicle.

5. The method as defined in claim 1, wherein the pharmacologically active basic agent is administered in the form of an acid addition salt with a pharmaceutically acceptable acid.

6. The method as defined in claim 5, wherein the acid is a fatty acid containing from about 6 to about 18 carbon atoms.

7. The method as defined in claim 5, wherein the acid is a fatty acid containing from about 6 to about 12 carbon atoms.

8. The method as defined in claim 1, wherein the amount of the fatty acid of medium chain length in the vehicle is substantialy the amount which is necessary to form an acid addition salt of the pharmacologically active basic agent and wherein the vehicle further comprises at least one glyceride selected from the group of mono- and diglycerides of fatty acids containing from about 6 to about 18 carbon atoms and mixtures thereof.

9. The method as defined in claim 1, wherein said administering step comprises enteral administration.

10. The method as defined in claim 1, wherein said administering step comprises topical administration.

11. The method as defined in claim 1, wherein said vehicle further comprises at least one free fatty acid containing from about 12 to about 18 carbon atoms.

12. The method as defined in claim 1, wherein said vehicle further comprises at least one glyceride selected from the group consisting of tri-, di-, and monoglycerides or mixtures thereof 13. The methods as defined in claim 12, wherein the glyceride is a fatty acid glyceride.

14. The methods as defined in claim 13, wherein the glyceride is selected from the group consisting of mono- and diglycerides of fatty acids and mixtures thereof.

15. The method as defined in claim 13, wherein the fatty acid within the glyceride comprises from about 6 to about 18 carbon atoms.

16. The method as defined in claim 13, wherein at least part of the fatty acids within the glycerides are saturated fatty acids.

17. The method as defined in claim 13, wherein at least part of the fatty acids within the glycerides are unsaturated fatty acids.

18. The method as defined in claim 13, wherein the fatty acids are selected from the group consisting of capric acid, caprylic acid, palmitic acid, stearic acid, and oleic acid.

19. The method as defined by claim 1, wherein said active agent comprises diazepam.

20. The method as defined by claim 1, wherein said active agent comprises 7-chlor-1-methyl-2-(hydroxymethyl)-5-(2'-chlorophenyl)-1H-2,3-dihydro-1,4-benzodiazepine.

21. The method as defined by claim 1, wherein said active agent comprises an aliphatic or heterocyclic amine group.

* * * * *